United States Patent [19]

Helle et al.

[11] Patent Number: 5,369,943
[45] Date of Patent: Dec. 6, 1994

[54] EQUIPMENT FOR PROVIDING A MEDICINE ROD WITH A SHELL

[75] Inventors: Timo Helle; Rolf Hartzell, both of Turku; Pekka Nieminen, Preitilä; Pekka Lankinen, Turku, all of Finland

[73] Assignee: Leiras Oy, Turku, Finland

[21] Appl. No.: 93,892

[22] Filed: Jul. 20, 1993

[30] Foreign Application Priority Data

Jul. 31, 1992 [FI] Finland .................. 923468

[51] Int. Cl.5 ............................................. A61J 3/07
[52] U.S. Cl. ...................................... 53/567; 53/385.1; 53/560; 53/900; 29/819
[58] Field of Search ................ 53/567, 560, 900, 547, 53/556, 454, 459, 471, 236, 385.1, 523, 79; 29/819; 604/890.1

[56] References Cited

U.S. PATENT DOCUMENTS

| | | | |
|---|---|---|---|
| 3,650,084 | 3/1972 | Moreland | 53/900 X |
| 3,977,060 | 8/1976 | Ishikawa | 29/819 X |
| 4,339,868 | 7/1982 | Mazzer | 29/819 X |
| 5,230,207 | 7/1993 | Hartzell et al. | 53/567 X |
| 5,317,849 | 6/1994 | Sauter | 53/900 X |

Primary Examiner—James F. Coan
Attorney, Agent, or Firm—Adduci, Mastriani, Schaumberg & Schill

[57] ABSTRACT

The invention relates to providing a medicinal rod with a shell. The shell is formed from a hose, which is expanded by pressurizing its inner space. The medicinal rod is pushed into the expanded hose, after which the pressure is relieved. The hose tightens over the rod after the pressure relief.

3 Claims, 6 Drawing Sheets

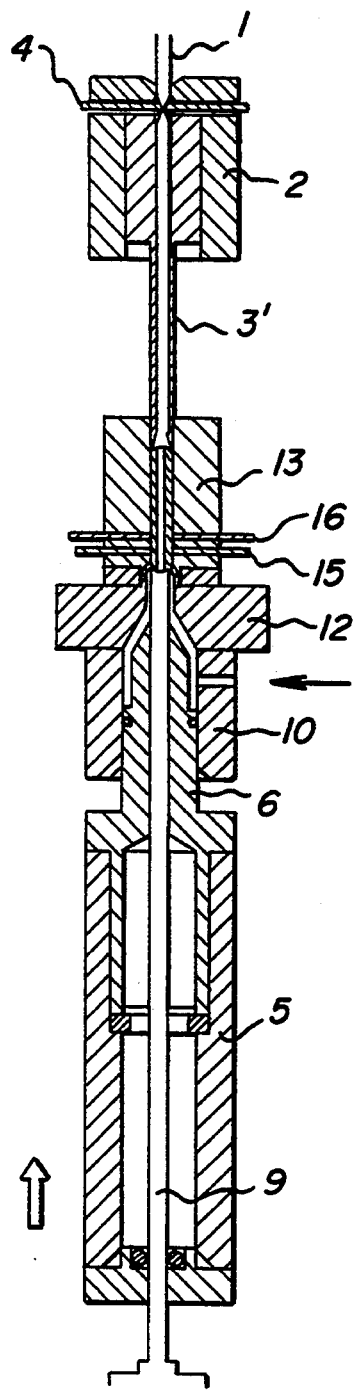
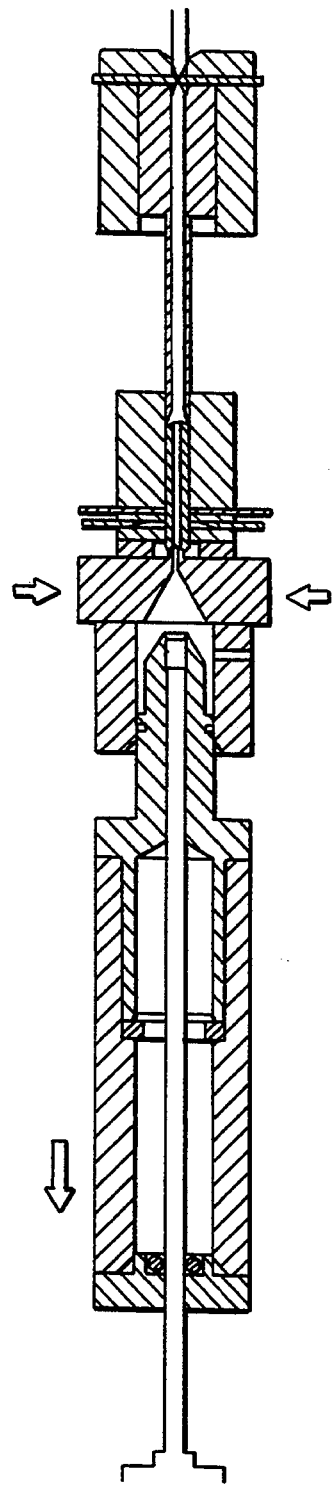
FIG. 5
FIG. 6

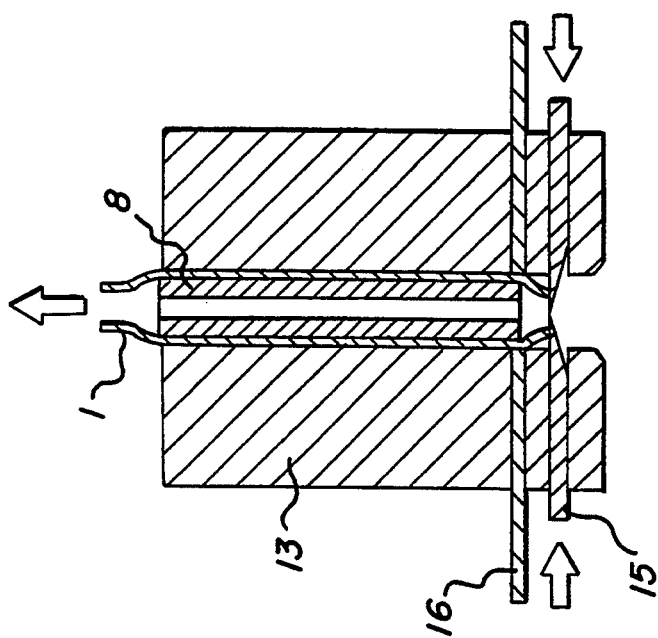
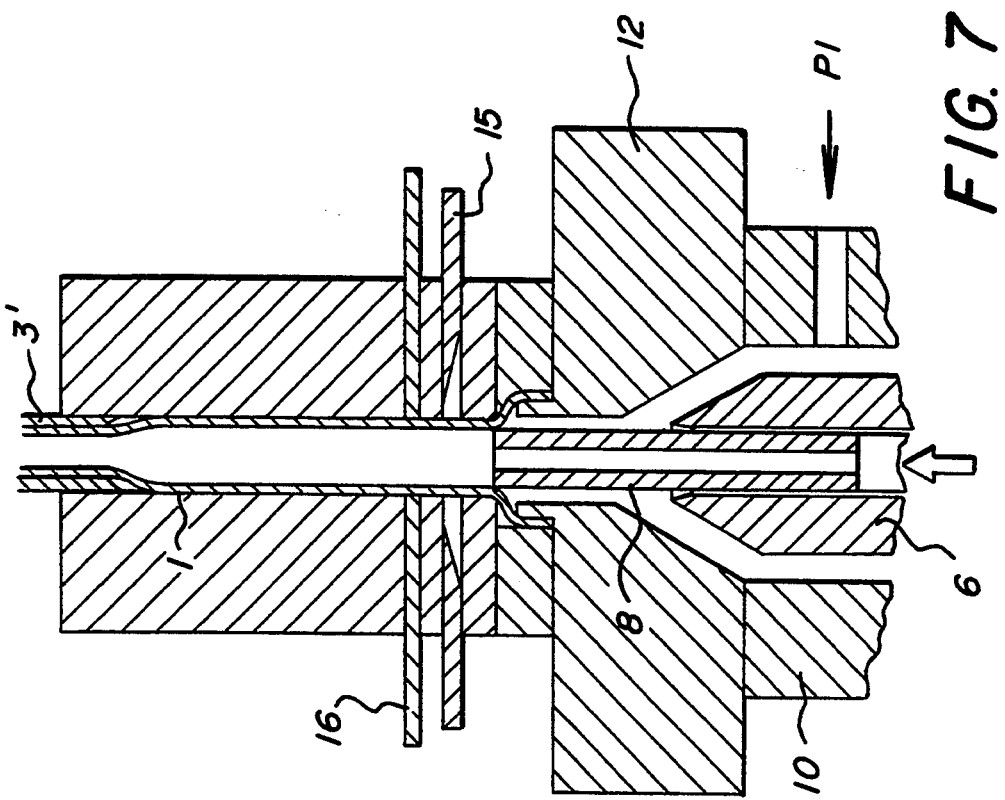

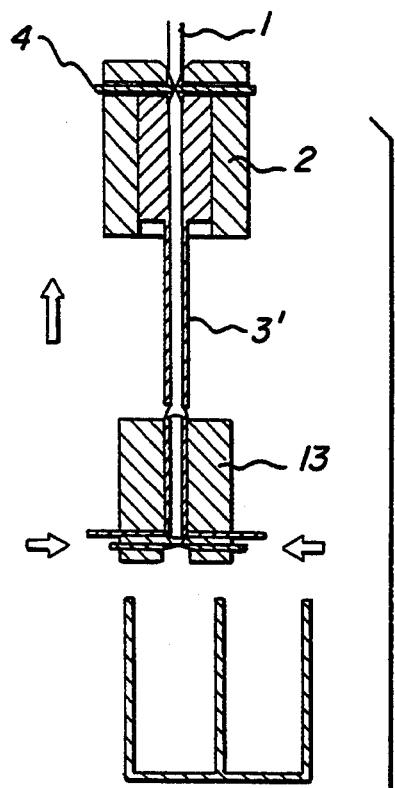 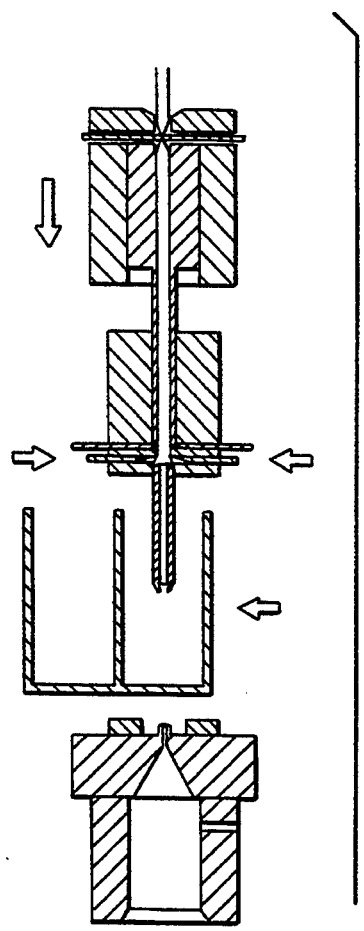
FIG. 9  FIG. 10
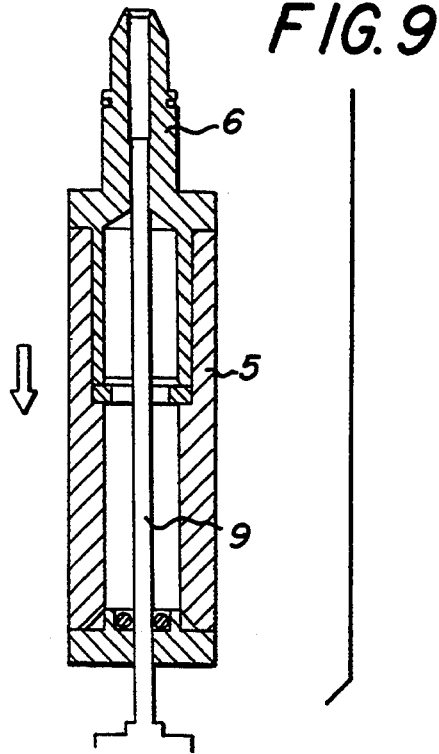 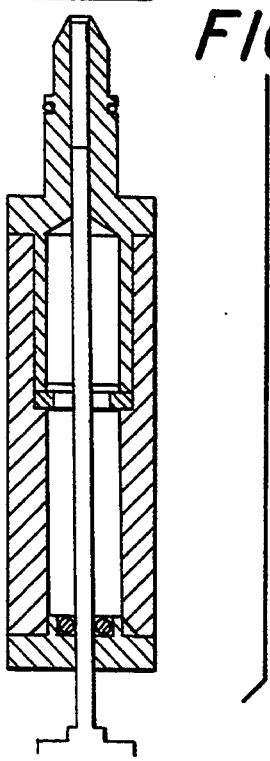

EQUIPMENT FOR PROVIDING A MEDICINE ROD WITH A SHELL

The present invention relates to an equipment for providing a medicinal rod with a shell. The medicinal rod may be comprised e.g. of a medicine embedded in a plastic material, which medicine is intended to diffuse from the plastic material carrier over a long period of time. The plastic material may be a silicone plastic and the medicine may be e.g. a contraceptive substance. For controlling the release of the medicine more accurately, the medicinal rod is provided with a shell, i.e. the medicine is encapsulated. Such a shell, which is comprised e.g. of silicone plastic, is tightened around the medicinal rod for achieving a proper capsule. Said capsule may be installed on a suitable fastener e.g. for inserting it inside the womb.

In the inventive equipment, the above-mentioned capsule provided with a shell is prepared by starting from a tubular or hose-like shell material, whose inner diameter is less than the outer diameter of the medicinal rod, as well as from a medicinal rod. In the equipment, the shell hose is expanded such that the medicinal rod may be inserted inside it, after which the shell hose is allowed to tighten over the inserted medicinal rod. In the equipment, the expansion of the shell hose has been achieved by blowing compressed air inside the hose.

The construction of the inventive equipment as well as its operation appear best on the basis of the accompanying drawing and on a description related thereto.

In the drawing:

FIG. 5 shows the equipment in a step, where the medicinal rod is inserted into the expanded shell hose;

FIG. 6 shows the equipment at the final step of the insertion of the medicinal rod;

FIG. 7 is a more detailed partial view of the initial step of the insertion of the medicinal rod;

FIG. 8 is a more detailed partial view of the finishing step of a coated medicinal capsule;

FIG. 9 shows the equipment in the finishing step of the medicinal capsule;

FIG. 10 shows the equipment in the extraction step of the medicinal capsule.

Figure 1:
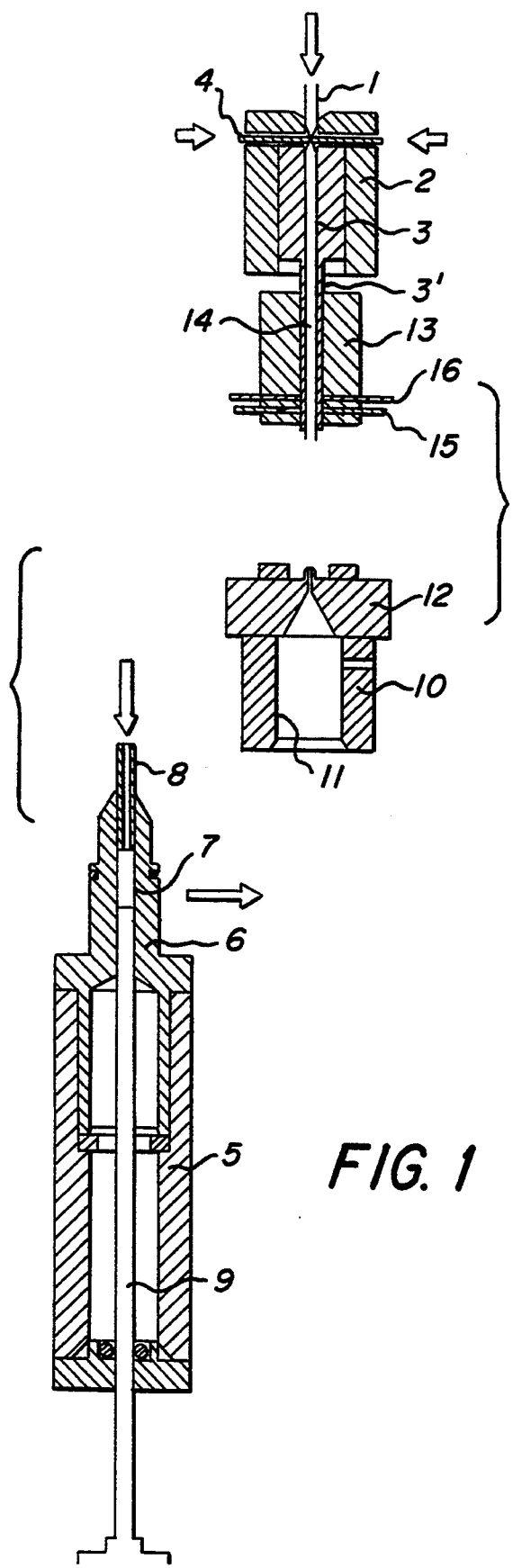
FIG. 1 shows the equipment at the start of an operating sequence, or in the insertion step of a shell hose and a medicinal rod to be encapsulated.

The equipment shown in the figures of the drawing comprises four basic parts, which are fitted to operate together to form a mantled capsule by starting from a shell hose 1 as well as from a fixed-size medicinal rod 8. The basic parts are a shell-hose feeder 2, a medicinal-rod inserter 5, an expander 10 and a connecting chamber 13.

The purpose of the shell-hose feeder 2 is to feed a hose-like shell blank forming the capsule shell in a fixed size to an equipment section, where the medicinal rod is inserted into this shell blank.

The medicinal rod to be encapsulated is in its part brought to the equipment by the medicinal-rod inserter 5, whose purpose is to deliver the medicinal rod into the expanded shell blank. A second purpose of this inserter 5 is to help in the forming of a flow channel, with which the compressed air expanding the shell blank is introduced.

In a close cooperation with the medicinal-rod inserter 5 is the expander 10, whose basic task is to achieve the expansion of the shell hose such that the medicinal rod supported by the inserter 5 may be pushed inside this. The expander forms a seat for an inserting nose 6 of the inserter 5, into which the inserter is dimensioned to set tightly. The bottom of the seat of the expander 10 is formed from expander jaws 12, whose purpose is to open the mouth of the shell hose and to form therefrom an inlet guide for the medicinal rod. On the other hand, the expander 10 forms part of a channel, via which the air is led to open the shell hose by the length of the medicinal rod, after the hose is expanded at its mouth area by means of the expander jaws 12.

Between the expander 10 and the shell-hose feeder 2 is located a device section, in which the actual connection of the medicinal rod with the shell blank hose occurs. This connecting chamber 13 is a section provided with a through-hole, which at its one end receives the shell hose and at its opposite end the medicinal rod to be inserted into the hose. The cutting elements of the shell hose are placed in this section, which cutting elements are also used for cutting the final capsule off the shell hose.

The detailed construction of different equipment parts as well as their mutual operation is described next.

The shell-hose feeder 2 is provided with a through-hole, whose diameter is dimensioned to correspond to the outer diameter of the shell hose 1. At the inlet end of the shell hose, the feeder is provided with clamps penetrating into the hole 3, which on one hand keep the hose forming the shell blank in place during different operating steps and are on the other hand closed in a step, when compressed air is supplied into it from the opposite end for expanding the hose. The opening extending through the feeder 2 has been extended at the discharge end of the feeder as a needle-like feed guide 3'. Said shell-hose feeder 2 is arranged to perform multistep reciprocating movements in the different stages of the capsule preparation, which movements and their purpose are described subsequently.

The medicinal rod to be mantled or encapsulated is led into the joining chamber from an opposite end relative to the inlet end of the hose forming the shell blank. The medicinal rod is brought with the inserter 5. This inserter has a inserting nose 6, which has been directed in the equipment towards the shell-hose feeder. This inserting nose is provided with an axial through-going hole 7, which is dimensioned according to the outer diameter of the medicinal rod 8 such that the medicinal rod may be pushed into this hole, and ejected therefrom to the encapsulation step. For pushing the medicinal rod out, the hole has a pusher 9 reciprocatively movable therein. For the inserter 5 is on the other hand arranged a transverse movement perpendicularly to its axial direction for picking up the medicinal rod as well as an axial reciprocating movement for delivering the medicinal rod.

The purpose of the expander 10 in the equipment is to guide the medicinal rod brought by the inserter 5 into the expanded shell hose and also to cause on its part deformations to the shell hose, which help the pushing of the medicinal rod into the shell hose. First of all, for this purpose, the expander is formed into a seat 11 for the inserting nose 6 of the inserter 5. On one hand, the bottom part of the seat of the expander 10 is provided with expander jaws 12, by means of which it is possible to expand the mouth of the shell hose and to guide the compressed air expanding the hose as well as the medicinal rod to be encapsulated into the hose. For this purpose, for the expander jaws 12 is arranged a reciprocating opening and closing movement, which is essentially perpendicular to the main axial direction of the equipment.

The actual encapsulation step of the medicinal rod is performed in the connector 13. This section is provided with a through-hole 14, whose diameter corresponds to the outer diameter of the needle-like feed guide 3' of the shell-blank feeder 2. The feeder brings by means of its feed guide a length of the shell hose, which is fitted to the length of the medicinal rod. After the feed guide has been drawn out of the connector, a space corresponding to the wall thickness of the feed guide remains therein for the expansion of the shell hose. The connector 13 is in cooperation with the expander 10 at its opposite end relative to the feeding end of the shell hose. The expander jaws 12 have spreader noses, which enter somewhat inside the mouth of the shell hose projecting from the connector 13. The noses open the hose mouth during the opening movement of the jaws. The connector 13 has also a cutting device 15, by means of which the coated capsule is finished and removed from the remaining shell hose.

The operation of the equipment will be next described with reference to the figures of the accompanying drawing.

During the entire encapsulation cycle, the only equipment part keeping its position is the expander 10, although part of it also performs a certain movement. The remaining parts perform movements in directions relative to each other and to the expander. As axial direction of the equipment is regarded in the following the longitudinal travelling direction of the shell hose through the equipment.

The initial situation of the cycle is shown in FIG. 1. The connector 13 is in the axial direction in its drawn away position relative to the expander 10, in connection with the blank-hose feeder 2, which is in its middlemost drawn-away position relative to the expander 10. The blank hose 1 is inserted into the connector and the hose clamps 4 in the blank-hose feeder 2 are closed.

The medicinal-rod inserter 5 is in a position drawn aside from the axial direction of the equipment as well as in a position drawn away from the expander 10 in the axial direction. In this position of the inserter 5, the medicinal rod 8 to be encapsulated is brought to the hole 7 in the inserting nose 6 of the inserter. The pushing rod 9 of the inserter is then in a withdrawn position.

Figure 2:
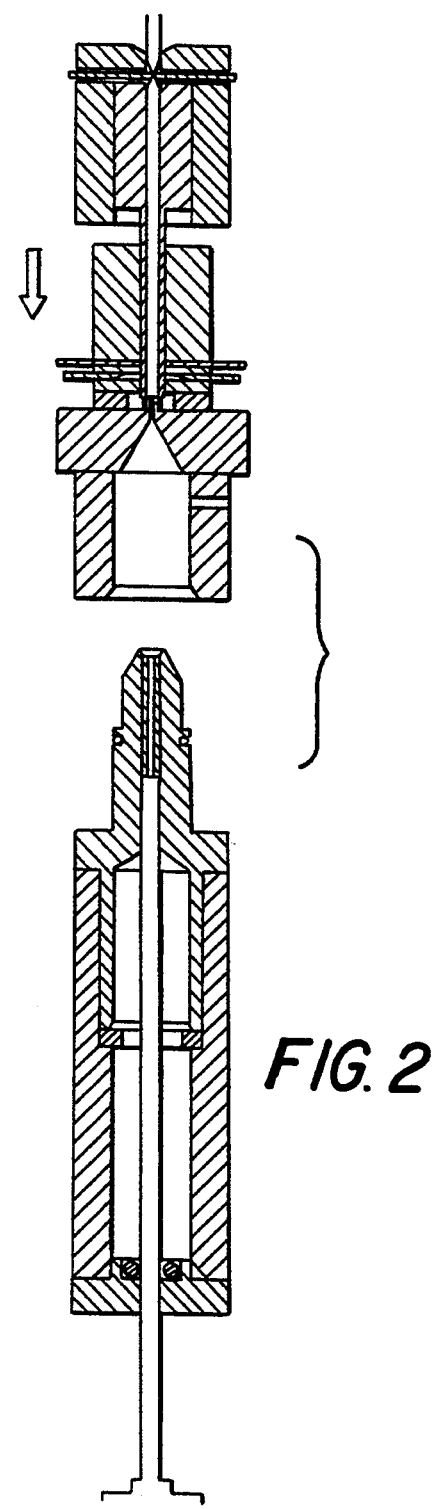
FIG. 2 shows the equipment in the following operating step, after a sufficient shell hose length has been fed in and when the medicinal rod to be encapsulated is in its positioner.

The next cycle step is shown in FIG. 2, in which the connector 13 as well as the feeder 2 have been brought together to the connection of the expander 10. In this step, the expander jaws 12 of the expander are closed against each other, and their noses penetrate into the inlet opening of the shell hose 1 brought by the connector 13. The clamps 4 of the feeder 2 are still closed to keep the hose 1 in position in the feeder 2 as well as in the connector 13. The inserter 5 is returned to the axial line.

Figure 3:
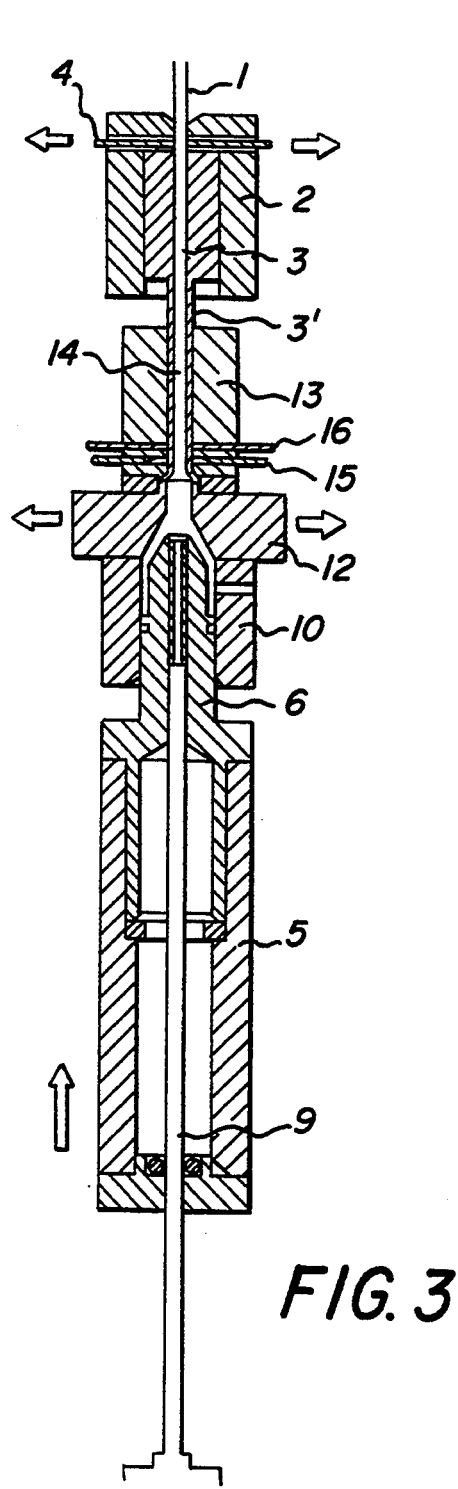
FIG. 3 shows the equipment in the initial situation of the insertion step of the medicinal rod.

In the next cycle step, which is shown in FIG. 3, the clamps 4 of the feeder 2 as well as the jaws 12 of the expander 10 are opened in a perpendicular direction to the axial direction. At the same time, the inserter 5 is brought axially to the expander 10, whereby its inserting nose 6 positions on the seat 11 of the expander. In this operating step, the inlet opening of the blank hose, which comes out of the hole 14 of the connector 13, is expanded by the jaws 12 of the expander 10. Furthermore, in this operative mode, as the jaws 12 are spacing apart, a flow channel opens between the nose 6 of the inserter and the jaws 12, via which channel the compressed air expanding the hose 1 may be led into the hose.

Figure 4:
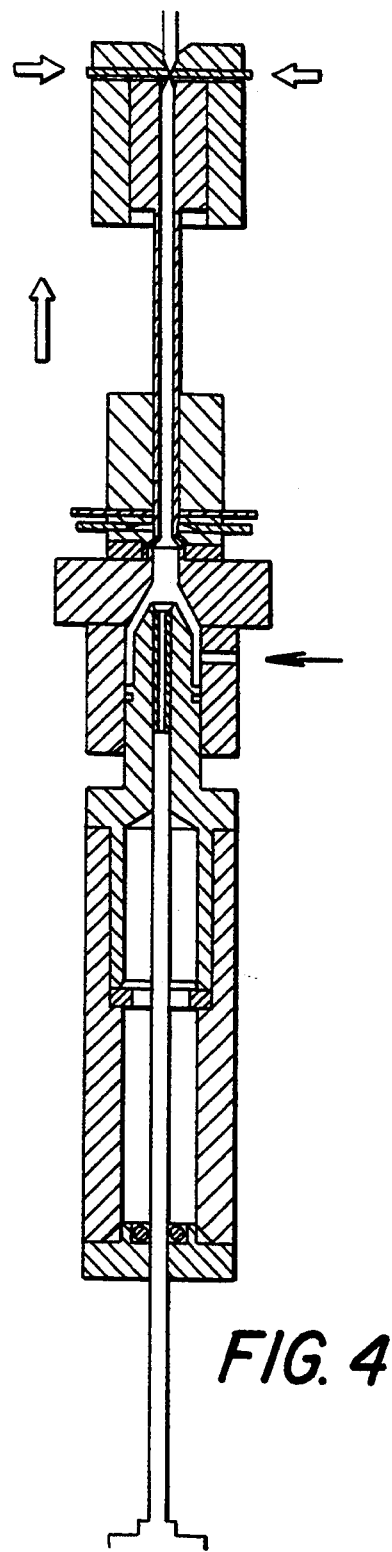
FIG. 4 shows the equipment in the expansion step of the shell hose by utilizing compressed air blown inside the hose.

In the operating step of FIG. 4, the feeder 2 moves away from the connector 13, whereby the feed guide 3' of the feeder 2 exits from the hole 14 of the connector 13 and leaves the hose 1 in a over-sized hole relative to its diameter. After the feeder 2 has moved away to its middlemost axial extreme position relative to the connector 13, the clamps 4 of the feeder 2 are closed. In this step, the compressed air to be supplied via the expander 10 is turned on and the pusher 9 of the inserter 5 is activated. The compressed air expands the hose in the hole 14 of the connector 13 for advancing movement of the medicinal rod 8 inserted by the pusher. After the medicinal rod 8 has been inserted to the working-stroke length of the pusher 9, which terminates just on the hole mouth of the connector 13, the pusher is drawn to its rear position and the jaws 12 of the expander 10 are returned to their initial position against each other, as shown in FIG. 6. The supply of compressed air led via the expander 10 is interrupted, and at the same time, the axial movement of the inserter 5 away from the expander is started.

The mantled capsule is finished and cut off the hose 1 according to FIGS. 9 and 10 such that the blank hose 1 is first drawn with the feeder 2, whose clamps 4 are closed, further inside the connector 13, until an optic sensor 16 in the connector detects the end of the medicinal rod 8. In this step, the cutter 15 in the connector 13 is activated, which trims the end of the mantled capsule. In the next step, the blank-hose feeder 2 is returned, the clamps 4 still in a closed position, towards its middlemost extreme position and towards the connector 13, whereby the hose 1 is pushed into the connector 13 and correspondingly the mantled capsule away from the connector. The pushing-out is monitored by an optic sensor 16, and the capsule is cut off the hose 1 on the basis of an information provided by the sensor. The equipment parts are then transferred to their positions according to FIG. 1, and the operating sequence may be repeated in the manner described above.

Figure 11:
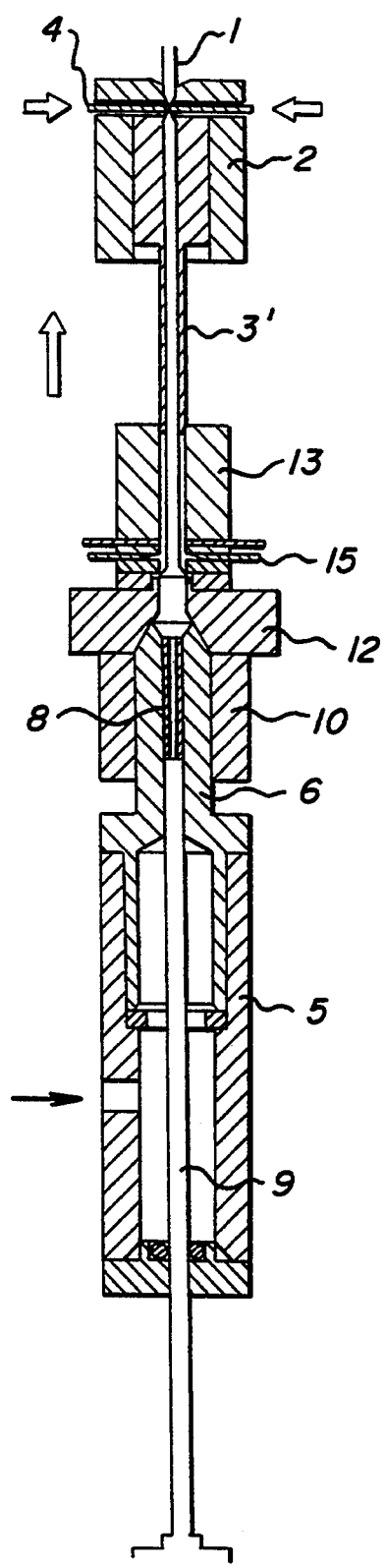
FIG. 11 is a view of an operating step corresponding to FIG. 4, related to an alternative equipment realization.

FIG. 11 shows a certain modification of the inventive equipment, in which there is an essential difference in the suppy of air expanding the blank hose 1. In this alternative, air is supplied through a hollow pusher 9. The alternative requires a hollow medicinal rod 8. In this alternative, the nose 6 of the inserter 5 does not have to be formed for an air flow channel.

We claim:

1. An equipment for providing a fixed-size medicinal rod (8) with a shell, by means of which equipment the medicinal rod is placed in a hose-like shell blank (1) and the shell blank is tightened into a shell around the rod, characterized in that the equipment comprises:

a feeder (2) for the shell hose (1), which is provided with a through-opening (3) for the shell hose of a continuous length, which through-opening continues on the outlet side of the feeder as a needle-like feed guide (3') exceeding the length of the medicinal rod to be encapsulated, as well as clamp elements (4) extending into the through-opening (3) on its inlet area for grasping the shell hose as well as for closing it, which feeder is arranged to perform a reciprocating axial feeding movement in the direction of the through-opening (3);

a medicinal-rod inserter (5), which is provided with an inserting nose (6) directed towards the shell-hose feeder (2), which nose has a through-opening (7) corresponding to the outer diameter of the medicinal rod as well as a pusher (9) arranged reciprocatively in the opening for discharging the medicinal rod (8) placed in the opening from the inserting nose towards the shell-hose feeder, which inserter (5) for receiving the medicinal rod is arranged to perform a reciprocating transverse movement relative to the direction of the through-opening (7), as well as a reciprocating axial movement in the direction of the through-opening (7) towards the feeder (2) as well as away therefrom for releasing the medicinal rod;

an expander (10), which is placed between the shell-hose feeder (2) and the medicinal-rod inserter (5) to cooperate with the medicinal-rod inserter and which is provided with an axial seat (11) corresponding to the outer diameter of the inserting nose (6) for receiving the inserting nose, the bottom of which seat is formed by expander jaws (12), which are arranged to move away from each other in a direction perpendicular to the axial direction of the seat and to be joined together correspondingly;

a connector (13), which is placed between the expander (10) and the shell-hose feeder (2) and which comprises a through-opening (14) for receiving a feed guide (3') of the shell-hose feeder (2), as well as cutting elements (15) for trimming the end of the shell coated capsule and for separating the capsule from the shell hose; and elements for supplying pressurized air to the connector (13) via the expander (10).

2. An equipment according to claim 1, characterized in that the pressurized air is arranged to be supplied to the connector (13) in a space between the inserting nose (6) in the seat of the expander (10) and the seat.

3. An equipment according to claim 1, characterized in that the pressurized air is arranged to be supplied to the connector (13) in a space via an opening (7) of the inserting nose (6) in the seat of the expander (10).

* * * * *